US009398881B2

(12) United States Patent
Davis et al.

(10) Patent No.: US 9,398,881 B2
(45) Date of Patent: Jul. 26, 2016

(54) MICRO-ANALYZER WITH PASSIVE AGGREGATOR

(71) Applicant: The Regents of the University of California, Oakland, CA (US)

(72) Inventors: Cristina Davis, Davis, CA (US); Hamzeh Bardaweel, Davis, CA (US); Konstantin Zamuruyev, Davis, CA (US); Jean-Pierre Delplanque, Davis, CA (US); Nicholas J. Kenyon, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 196 days.

(21) Appl. No.: 14/372,438

(22) PCT Filed: Jan. 25, 2013

(86) PCT No.: PCT/US2013/023236
§ 371 (c)(1),
(2) Date: Jul. 15, 2014

(87) PCT Pub. No.: WO2013/112898
PCT Pub. Date: Aug. 1, 2013

(65) Prior Publication Data
US 2015/0013439 A1    Jan. 15, 2015

Related U.S. Application Data

(60) Provisional application No. 61/590,694, filed on Jan. 25, 2012.

(51) Int. Cl.
*G01N 1/00* (2006.01)
*G01N 33/497* (2006.01)
(Continued)

(52) U.S. Cl.
CPC ............... *A61B 5/4845* (2013.01); *A61B 5/083* (2013.01); *A61B 10/0045* (2013.01);
(Continued)

(58) Field of Classification Search
CPC .................... A61B 5/4845; G01N 2001/2244; G01N 2001/2282; G01N 1/4022; G01N 2001/4033; G01N 2001/002; G01N 2035/1034
See application file for complete search history.

(56) References Cited

U.S. PATENT DOCUMENTS 6,043,878 A * 3/2000 Gratzl ................. B01F 13/0071
356/246
7,632,388 B2 * 12/2009 Rikihisa .................... B01F 3/08
204/600

(Continued)

FOREIGN PATENT DOCUMENTS

DE    10310615 B3    11/2004
EP    0317987 A2    5/1989
(Continued)

*Primary Examiner* — Daniel J Colilla
*Assistant Examiner* — Ruben Parco, Jr.
(74) *Attorney, Agent, or Firm* — Park, Vaughan, Fleming & Dowler LLP; Laxman Sahasrabuddhe

(57) ABSTRACT

A micro-analyzer is described. This micro-analyzer includes an outer surface region on a sampler surface that receives liquid droplets, and aggregates and moves the droplets radially toward an inner surface region on the sampler surface that receives the droplets. For example, the outer surface region may include a set of micro-patterned concentric rings, each of which includes a set of radially oriented wall-groove pairs. Moreover, the sampler surface may be increasingly less hydrophobic along a radial direction toward the center of the sampler surface, thereby creating an axisymmetric wettability gradient. After the droplets are aggregated, an analysis mechanism in an area within the inner surface region performs analysis on the aggregated droplets.

12 Claims, 4 Drawing Sheets

(51) Int. Cl.
*A61B 5/00* (2006.01)
*G01N 21/03* (2006.01)
*A61B 5/083* (2006.01)
*A61B 10/00* (2006.01)
*G01N 1/22* (2006.01)
*G01N 1/40* (2006.01)

(52) U.S. Cl.
CPC ............. *G01N 1/4022* (2013.01); *G01N 21/03* (2013.01); *G01N 33/497* (2013.01); *G01N 1/2202* (2013.01); *G01N 2001/002* (2013.01); *G01N 2001/2282* (2013.01); *G01N 2001/4033* (2013.01); *G01N 2021/035* (2013.01)

(56) References Cited

U.S. PATENT DOCUMENTS

| | | | |
|---|---|---|---|
| 9,157,842 B1 * | 10/2015 | Ancona | B01D 53/0462 |
| 2005/0150277 A1 * | 7/2005 | Janesky | F24F 3/14 73/73 |
| 2011/0194084 A1 * | 8/2011 | Riepen | G03F 7/70341 355/30 |

FOREIGN PATENT DOCUMENTS

| | | | |
|---|---|---|---|
| JP | 2005331410 A | * 12/2005 | ............. G01N 35/08 |
| JP | 2008157708 A | 7/2008 | |
| TW | 200842360 A | 11/2008 | |

* cited by examiner

MICRO-ANALYZER WITH PASSIVE AGGREGATOR

BACKGROUND

1. Field

The present disclosure generally relates to a micro-analyzer. More specifically, the present disclosure relates to a micro-analyzer with a passive aggregator for aggregating liquid droplets.

2. Related Art

Exhaled human and animal breath analysis has become attractive as a diagnostic tool, for example, for various diseases including: cancer, asthma, and respiratory infections. One of the technological challenges for collecting exhaled breath samples from subjects is the design of an efficient and reliable breath sampler. Existing breath-sampling techniques for collecting exhaled breath are typically power hungry, bulky, and have wide variability in performance (such as reproducibility and reliability). Moreover, the breath samples collected using the existing breath-sampling techniques are usually manually processed, which increases the risk of contamination and handling errors.

Hence, what is needed is a micro-analyzer without the problems described above.

SUMMARY

One embodiment of the present disclosure provides a micro-analyzer. This micro-analyzer includes: a substrate; and a sampler surface disposed on the substrate that receives liquid droplets. Moreover, the sampler surface includes: an outer surface region that facilitates aggregating and moving the droplets radially toward a center of the sampler surface; and an inner surface region, within the outer surface region, which receives the droplets collected by the outer surface region. Furthermore, the inner surface region includes an area with an analysis mechanism configured to analyze the droplets received at the inner surface region.

Note that the sampler surface may be increasingly less hydrophobic along a radial direction toward the center of the sampler surface. For example, the outer surface region may be micro-patterned to create a wettability gradient which is distributed axisymmetrically. (Alternatively, the wettability gradient may be distributed non-symmetrically.) Moreover, the wettability gradient may increase in an inward radial direction.

In some embodiments, the outer surface region is micro-patterned to create a wettability gradient which is distributed as a space-filled geometric hierarchically repeating pattern or which is distributed as a space-filled fractal pattern.

Furthermore, the outer surface region may include a set of micro-patterned concentric rings. A given micro-patterned concentric ring may include a set of radially oriented wall-groove pairs. For example, a wall within a given wall-groove pair may have a trapezoidal cross-section when viewed from above, and/or a base of the wall may have a varying width which increases in the inward radial direction.

In some embodiments, the number of wall-groove pairs in the given micro-patterned concentric ring increases from the outermost ring toward the innermost ring. For example, the number of wall-groove pairs may increase as a result of a decreasing width of the grooves from the outermost ring toward the innermost ring. Alternatively, the number of wall-groove pairs may increase as a result of a decreasing width of the grooves from one side of a non-symmetrically configured device to another. Note that the number of micro-patterned rings may control a wettability gradient of the outer surface region.

In some embodiments, the sampler surface receives a gas-phase or vapor-phase sample that condenses into the liquid droplets. In particular, the outer surface region may facilitate condensing at least a component in the received gas-phase sample into liquid-phase droplets on the sampler surface.

Additionally, the micro-analyzer may include a hydrophobic coating disposed on the outer surface region (and/or the inner surface region) to facilitate drop-wise condensation. This hydrophobic coating may include a super-hydrophobic thin film.

In some embodiments, the micro-analyzer includes an active condensation mechanism that continuously cools the sampler surface to facilitate drop-wise condensation. Alternatively or additionally, the active condensation mechanism may adaptively cool the sampler surface to facilitate selected condensation of pre-defined biomarkers within certain temperature regimes. For example, the active condensation mechanism may include a thermoelectric cooler.

Note that the substrate may be circular or non-circular. Moreover, the substrate may include silicon or a material other than silicon.

In some embodiments, the gas-phase sample includes a breath sample that includes at least a gaseous-phase component and/or an aerosolized droplet (which may include non-volatile compounds).

Another embodiment provides a method for analyzing droplets using the micro-analyzer.

Figure 1:
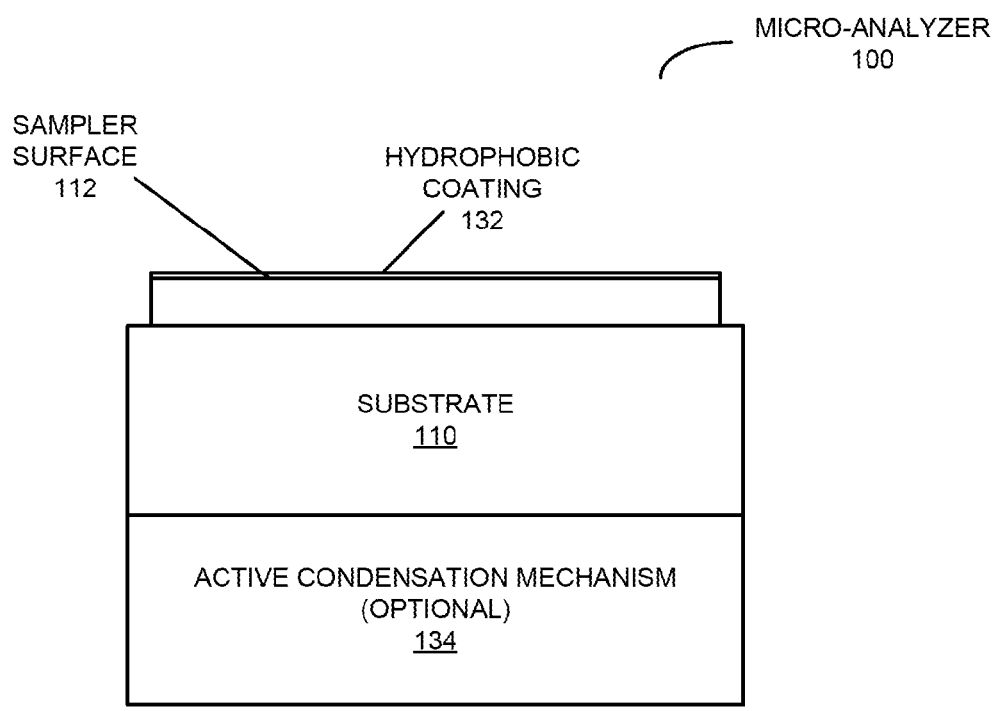
FIG. 1 is a block diagram illustrating a side view of a micro-analyzer in accordance with an embodiment of the present disclosure.
Figure 2:
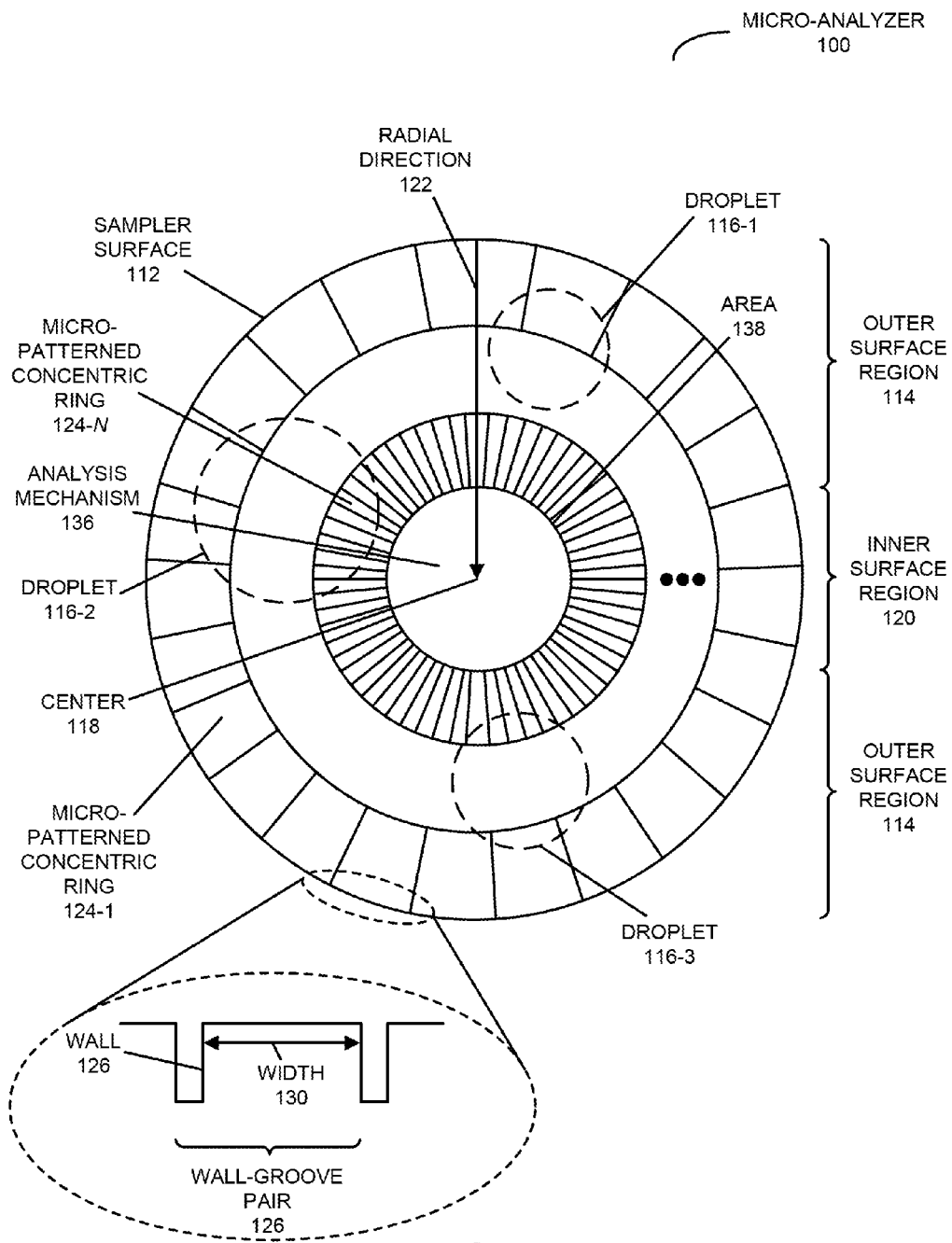
FIG. 2 is a block diagram illustrating a top view of the micro-analyzer of FIG. 1 in accordance with an embodiment of the present disclosure.

Table 1 provides the geometry and static contact angles for sets of micro-patterned concentric rings in the micro-analyzer of FIGS. 1 and 2 in an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

Embodiments of a micro-analyzer and a method for analyzing droplets using the micro-analyzer are described. This micro-analyzer includes an outer surface region on a sampler surface that receives liquid droplets, and aggregates and moves the droplets radially toward an inner surface region on the sampler surface that receives the droplets. For example, the outer surface region may include a set of micro-patterned concentric rings, each of which includes a set of radially oriented wall-groove pairs. Moreover, the sampler surface may be increasingly less hydrophobic along a radial direction toward the center of the sampler surface, thereby creating an axisymmetric wettability gradient. After the droplets are aggregated, an analysis mechanism in an area within the inner surface region performs analysis on the aggregated droplets.

The micro-analyzer may facilitate portable, energy-efficient gas-phase samplers, such as exhaled breath samplers, with high reproducibility and reliability. For example, the outer surface region may facilitate condensing at least a component in a received gas-phase sample into liquid-phase droplets on the sampler surface, which are then collected and analyzed by the analysis mechanism. Moreover, the micro-analyzer may be fabricated with high yield and low cost. Furthermore, the integrated micro-analyzer may eliminate the need for manual processing of the droplets, which may reduce or eliminate the risk of contamination and handling errors.

We now describe embodiments of a micro-analyzer. FIG. 1 presents a block diagram illustrating a side view of a micro-analyzer 100. This micro-analyzer includes: a substrate 110; and a sampler surface 112 (such as a patterned surface) disposed on substrate 110 that receives liquid droplets 116 (FIG. 2). For example, droplets 116 (FIG. 2) may be provided using a dropper or a pipette.

Moreover, as shown in FIG. 2, which presents a top view of micro-analyzer 100, sampler surface 112 includes: an outer surface region 114 that facilitates aggregating and moving droplets 116 radially toward a center 118 of sampler surface 112; and an inner surface region 120, within outer surface region 114, which receives droplets 116 collected by outer surface region 114.

Note that sampler surface 112 may be increasingly less hydrophobic along a radial direction 122 toward center 118 of sampler surface 112. For example, outer surface region 114 may be micro-patterned to create a wettability gradient which is distributed axisymmetrically. (Alternatively, the wettability gradient may be distributed non-symmetrically.) Moreover, the wettability gradient may increase in an inward radial direction. In some embodiments, outer surface region 114 is micro-patterned to create a wettability gradient which is distributed as a space-filled geometric hierarchically repeating pattern or which is distributed as a space-filled fractal pattern.

Furthermore, outer surface region 114 may include a set of micro-patterned concentric rings 124. A given micro-patterned concentric ring (such as micro-patterned concentric ring 124-1) may include a set of radially oriented wall-groove pairs (such as wall-groove pair 126). For example, a wall 128 within a given wall-groove pair may have a trapezoidal cross-section when viewed from above, and/or a base of wall 128 may have a varying width 130 which increases in the inward radial direction. Thus, in some embodiments the width 130 increases towards the center of sampler surface 112. This increase in area may provide the wettability gradient.

In some embodiments, the number of wall-groove pairs in the given micro-patterned concentric ring increases from outermost ring 124-1 toward innermost ring 124-N. For example, the number of wall-groove pairs may increase as a result of a decreasing width 130 of the grooves from outermost ring 124-1 toward innermost ring 124-N. Alternatively, the number of wall-groove pairs may increase as a result of a decreasing width 130 of the grooves from one side of a non-symmetrically configured device to another. Note that the number of micro-patterned rings may control a wettability gradient of outer surface region 114.

Additionally, micro-analyzer 100 may include analysis mechanism 136 in an area 138 in inner surface region 120. This analysis mechanism may analyze the aggregated droplets. For example, micro-analyzer 100 may perform on-chip micro-analysis. In particular, analysis mechanism 136 may perform a wide variety of analysis techniques, including: chemical analysis techniques (such as gas chromatography, mass spectrometry, chemical detection, etc.), materials analysis techniques, protein analysis techniques and blood-cell analysis techniques (such as blood cytology). While FIG. 2 illustrates an analysis mechanism integrated in micro-analyzer 100, in other embodiments the analysis mechanism may be external to micro-analyzer 100. In this way, micro-analyzer 100 may be used in conjunction with a variety of analyzers, including those provided by third parties.

In some embodiments, sampler surface 112 receives a gas-phase sample that condenses into liquid droplets 116. In particular, outer surface region 114 (and/or inner surface region 120) may facilitate condensing at least a component in the received gas-phase sample into liquid-phase droplets on sampler surface 112. These droplets may then be passively aggregated and moved towards analysis mechanism 136.

Referring back to FIG. 1, micro-analyzer 100 may include a hydrophobic coating 132 disposed on outer surface region 114 (FIG. 2) and/or inner surface region 120 (FIG. 2) to facilitate drop-wise condensation in embodiments where a gas-phase sample is received. This hydrophobic coating may include a super-hydrophobic thin film (which may have a contact angle with water greater than 150°).

In some embodiments, micro-analyzer 100 includes an optional active condensation mechanism 134 that continuously cools sampler surface 112 to facilitate drop-wise condensation. Alternatively or additionally, optional active condensation mechanism 134 may adaptively cool sampler surface 112 to facilitate selected condensation of pre-defined biomarkers within certain temperature regimes or ranges. For example, optional active condensation mechanism 134 may include a thermoelectric cooler.

Note that substrate 110 may be circular or non-circular. For example, while a rotationally symmetric geometry is illustrated in FIGS. 1 and 2, in other embodiments sampler surface 112 may include micro-patterned trenches arranged in a rectangular geometry. Moreover, substrate 110 may include silicon or a material other than silicon. Therefore, in some embodiments substrate 110 includes a material such as: glass, silicon, a ceramic, and/or a plastic (for example, substrate 110 may be fabricated using injection-molded plastic). In some embodiments, micro-analyzer 100 is a passive component.

Micro-analyzer 100 may be used in a wide variety of applications, including: power-generating systems, thermal management (such as cooling of electronics), two-phase flow devices, self-cleaning devices, environmental ambient sampling (such as detection of aerosols, pathogens and/or chemicals in the atmosphere), micro-fluidics, forensics, breath-sample collection for drug testing (including drunk driving, use of prescription medication, use of recreational or illicit, drugs, use of drugs or abuse such as cocaine, marijuana or methamphetamine, etc.), and biological-sample collection for use in medical testing. For example, the medical testing may be associated with a disease, such as: an infection, asthma, tuberculosis, chronic obstructive pulmonary disease, chronic respiratory disease, cancer, liver disease, etc. More generally, the medical testing may be used to monitor or assess the metabolism of an individual, including non-disease monitoring.

Other applications include assessing: the exposure of an individual to exogenous materials, chemicals or toxins (including those that are ingested, absorbed through the skin or breathed in); an individual's or an animal's metabolism of a specific drug or chemical; stress biomarkers associated with a psychological state (such as whether an individual is lying or is mentally ill); physiological biomarkers associated with reproduction (such as hormones); compliance of an individual with a medication regime (such as, did the individual take their medicine at the appropriate times); whether a prescribed medication is at therapeutic dose); intentionally ingested taggants or tracking compounds (which may be used to identify and/or authenticate an individual); biometric identification; and/or biomarkers related to sensitivity of an individual to operating conditions (such as a susceptibility to poor performance at high altitude or alertness). For example, this approach may be used to assess dietary or travel habits of an individual based on the chemicals detected in the breath. Alternatively, this approach may be used to assess the short- and long-term effects of radiation exposure. In some embodiments, micro-analyzer 100 is used in a single point-of-care device (such as a 'lab on a chip') that is used to diagnose or monitor the health of an individual, an animal or a plant.

In an exemplary embodiment, micro-analyzer 100 is used to condense, transport and aggregate droplets 116 (FIG. 2) from a breath sample received from an individual (i.e., the gas-phase sample includes a breath sample that includes at least a gaseous-phase component and/or an aerosolized droplet that may include non-volatile compounds). In particular, micro-analyzer 100 includes a microelectromechanical system (MEMS)-based exhaled breath sampler for the capture of both volatile and non-volatile biomarker metabolites. The surface of the sampler (for example, sampler surface 112) may promote drop-wise condensation, and may enable a free-energy-driven mechanism to collect exhaled breath condensate from the surface. For example, drop-wise condensation may be enhanced by making the surface of the sampler superhydrophobic. Note that drop-wise condensation may be preferable over film-wise condensation because it allows one order of magnitude larger coefficients of heat transfer between the surface and the exhaled breath.

Moreover, the surface of the sampler may be patterned with a radially-distributed wettability gradient that provides a free-energy-driven mechanism to route exhaled breath condensate droplets toward a central collection point. Therefore, the transport of the droplets on the surface may be passive (i.e., a power source may not be used to transport the droplets on the surface). Furthermore, the wettability gradient may contribute to maintaining drop-wise condensation on the sampler surface by continuously removing droplets from the surface, and thus freeing prior nucleation sites for new droplets to nucleate.

The wettability of a flat surface is described by Young's Equation $$\cos(\theta_e) = \frac{\gamma_{SV} - \gamma_{SL}}{\gamma_{LV}}, \quad (1)$$

where $\theta_e$ is the equilibrium contact angle and, $\gamma_{SV}$, $\gamma_{SL}$, and $\gamma_{LV}$ are, respectively, the solid-vapor, solid-liquid, and the liquid-vapor interfacial free energies per unit area. By assuming that a liquid completely fills grooves of a rough surface, the contact angle of a droplet on a rough surface may be modeled as $$\cos(\theta_r^W) = r \cdot \cos(\theta_e), \quad (2)$$

where r is a roughness factor defined as the ratio of an actual area of the rough surface to a projected area. Alternatively, by assuming that the liquid is completely suspended by the grooves, the contact angle of a droplet on a rough surface may be modeled as $$\cos(\theta_r^C) = f_s \cdot (1 + \cos(\theta_e)) - 1, \quad (3)$$

where $f_s$ is the ratio of the area of the rough surface contacting the droplet to the projected area.

As noted previously, the presence of a surface wettability gradient induces net mass transport of droplets. In particular, a droplet tends to move toward the more wettable side if it experiences an imbalance in capillary forces across its edges, i.e., across the two opposite sides of the liquid-solid contact lines. Wettability gradients can be used to remove droplets from the surface by creating a spatial variation in the physical or chemical properties of the surface. As the droplet moves along the surface, a resistance force is developed typically attributed to the presence of local defects. In a tilted-surface experiment in which a droplet is deposited on an initially horizontal plate and the plate tilted until the droplet is just about to start moving, the force balance provides a measure of contact-angle hysteresis. In particular, the contact-angle hysteresis may be specified by the resistance force $$\cos(\theta_R) - \cos(\theta_A) = \frac{m \cdot g \cdot \sin(\alpha)}{\varpi \cdot \gamma_{LV}}, \quad (4)$$

where contact-angle hysteresis ($\theta_R - \theta_A$) is defined as the difference between receding $\theta_R$ and advancing $\theta_A$ contact angles, g is the acceleration of gravity, $\alpha$ is the minimum angle of tilt at which a droplet will spontaneously move, and m and $\omega$ are, respectively, the mass and width of the droplet base. Thus, a successful, free-energy driven droplet transport on a roughened surface may be achieved by creating an imbalance in capillary forces across the edges of the droplet, and minimizing contact-angle hysteresis.

While drop-wise condensation may be the preferred regime of condensation because of its higher rate of heat transfer compared to the film-wise condensation, initiating and maintaining drop-wise condensation is often challenging. For example, initiating drop-wise condensation usually requires non-wettable surfaces. In addition, maintaining drop-wise condensation usually requires continuous removal of small droplets from the surface. In contrast, during film-wise condensation the condensed liquid tends to wet the surface, and a film of liquid is formed on the surface by coalescence of the droplets. However, the presence of the liquid film typically significantly reduces heat transfer across the surface. As a consequence, the rate of condensation typically decreases as well.

In configurations where wettability is poor, the formation of a liquid film may be impeded, and the surface may be covered with a distribution of droplets with various sizes. This is drop-wise condensation. In this regime, heat transfer between the surface and the humid air may only be effected where droplets are present. Larger droplets, such as those with diameters greater than 10 µm, have a large thermal resistance and, thus, behave locally like a liquid film, which can significantly hinder heat transfer. Therefore, drop-wise condensation often can quickly turn into film-wise condensation, reducing the effectiveness of heat transfer and thus the condensation process. The super-hydrophobic thin film and/or the micro-patterned rings in the outer surface region on the surface of the sampler may be designed to prevent these challenges by initiating and maintaining drop-wise condensation.

Figure 3:
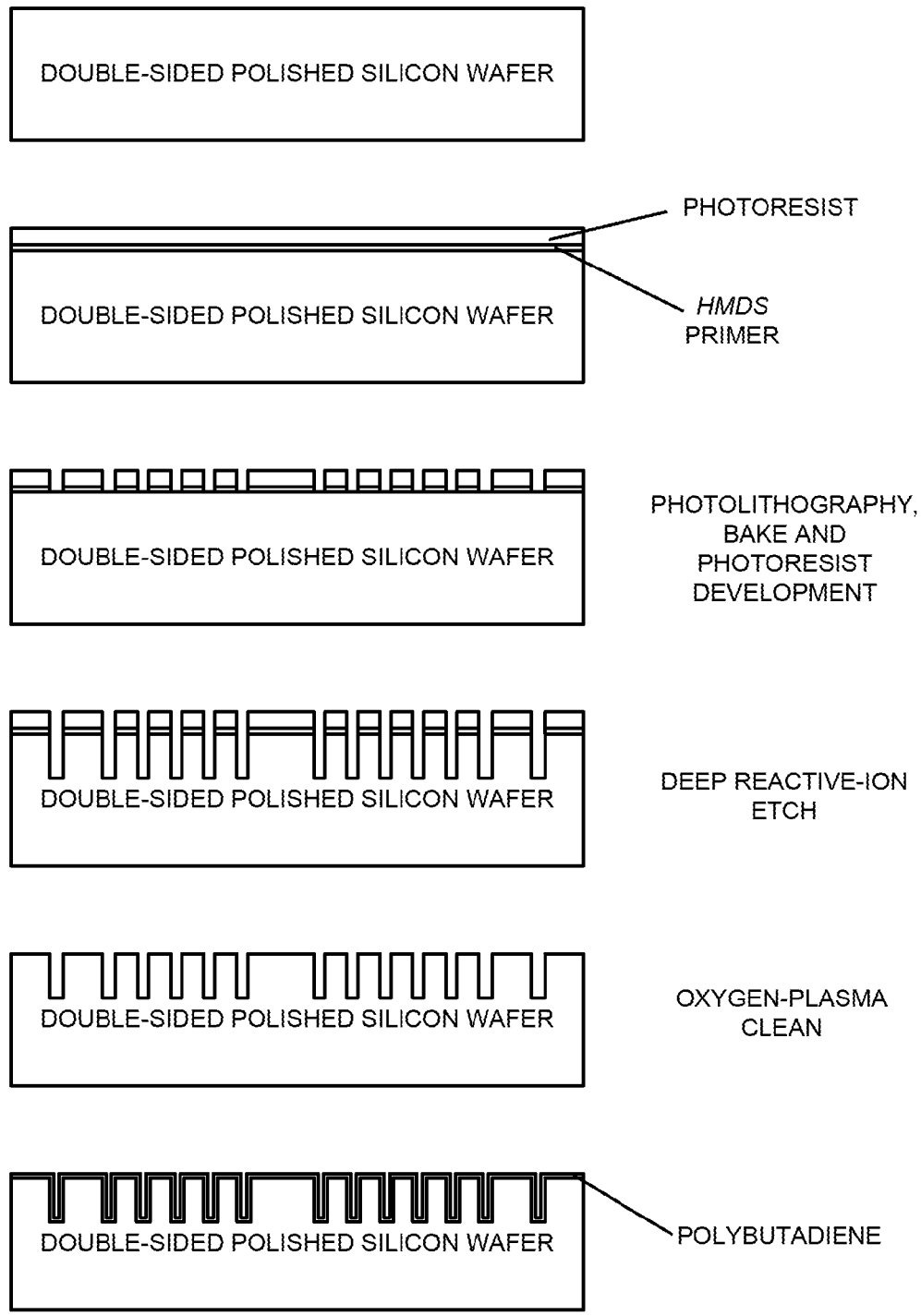
FIG. 3 is a flow diagram illustrating fabrication of the micro-analyzer of FIGS. 1 and 2 in accordance with an embodiment of the present disclosure.

We now describe techniques for fabricating the micro-analyzer. In general, both chemical composition and physical roughness of the surface contribute to its wettability. In the micro-analyzer, the surface may be patterned with micro-fabricated features, namely etched grooves or the micro-patterned rings, to increase its hydrophobicity. The wettability gradient may be obtained by gradually varying the roughness of the micro-patterned surface. Moreover, the surface may be subsequently coated with a low-energy interface material to make it super-hydrophobic. In an exemplary embodiment, silicon is used as the material of the sampler surface because of its high thermal conductivity and its adaptability with micro-fabrication techniques. Note that the surface may be patterned using contact photolithography, and deep reactive-ion etching may be used to etch the characteristic groove/ridge structure. The widths of the ridges and grooves may be varied to modulate the surface wettability. For example, the widths of the ridges and grooves may be changed radially to establish a wettability gradient in the radial direction of the sampler geometry. Next, the surface of the sampler may be spin-coated with a solution of polybutadiene dissolved in toluene, which is then annealed in a vacuum to remove entrapped solvent. Furthermore, the coated surface may be plasma treated in a vacuum chamber to create a plasma-fluorinated polybutadiene film. The fabrication of micro-analyzer 100 (FIGS. 1 and 2) is summarized in FIG. 3.

In an exemplary embodiment, a double-sided polished <100> silicon wafer is baked at 110 C for 12.5 minutes to remove water moisture. Then, the wafer is spin-coated with an adhesive layer of hexamethyldisilazane (HMDS) primer followed by a photoresist, such as MEGAPOSIT™ SPR™ 220 TM-7 photoresist (from Rohm and Hass Company of Philadelphia, Pa.). Moreover, the wafer is soft-baked at 105 C for 360 sec. Next, the wafer is patterned with the pre-defined micro-features using contact photolithography. To degas nitrogen from the wafer, a three-hour delay is allowed, followed by baking the wafer at 105 C for 300 sec. After a 45-minute delay, the wafer is softly agitated for 10-12 minutes in a developer, such as CD-26. The micro-features are then etched using a deep reactive-ion etcher.

In order to minimize the hysteresis and ease the transport of droplets on the prepared surface, cleanness of the wafer may be maintained during each operation in the surface coating process. For example, the wafer may be cleaned with acetone, dried with nitrogen, and further cleaned using oxygen plasma for 5 minutes. Polybutadiene having a molecular weight of 420 000, 36% cis 1,4 addition, 55% trans 1,4 addition, and 9% 1,2 addition (from the Sigma-Aldrich Company, LLC of St. Louis, Mo.) is dissolved in Touline (99.5% purity) at concentration of 5% (w/w). The wafer is then spin-coated with the prepared solution at 2000 rpm for 60 seconds. Next, the thin film is annealed in a vacuum oven for 1 hour at 900 C to remove entrapped solvent. The surface is plasma treated in a vacuum chamber for ten minutes. Prior to each plasma treatment, the chamber may be scrubbed with isopropanol followed by further cleaning using oxygen plasma at 200 Watts for 15 minutes. Furthermore, the wafer is placed inside the chamber, and the chamber is pumped down to its base pressure of 25 mTorr. CF4 gas is then admitted into the chamber, and the electrical discharge ignited. The plasma fluorination is carried out at 150 mTorr, 60 Watts, and 3.0 sccm CF4 flow rate for ten minutes. The plasma-fluorinated polybutadiene film is then cured in a vacuum oven for one hour at 900 C.

The resulting sampler surface may be micro-patterned with a series of concentric regions. Each region may include a periodic arrangement of radially patterned ridges and grooves with the density of ridges and grooves increasing (i.e., the widths of ridges and grooves decreasing) toward the center of the surface. Thus, the surface roughness may be tuned by increasing the number of walls and grooves toward the center. While the desired contact-angle distribution may be increasingly less hydrophobic toward the collection point, note that it may not be linear for a droplet to move on the surface. In particular, the droplet movement along the wettability gradient may be enhanced by the increasing difference between subsequent contact angles as the size of the micro-patterns decreases. Thus, the decreasing sensitivity of the droplet as the size of the micro-features decreases may be compensated for by an increasing difference in the contact angle. In addition, note that the wettability gradient may be distributed not only in a discrete manner from one micro-patterned region to the other, but also along the length of each region. This continuous distribution may be achieved by using trapezoidal geometry, with the wide base oriented toward the inner edge for the micro-patterns on each region. The resulting non-linear distribution of wettability gradient and the use of trapezoidal geometry for the micro-patterns may provide a successful self-cleaning property, which may collect at least 7% more condensate than a plain hydrophobic surface with the same dimensions. For example, the micro-analyzer may collect 50 µL of condensate from exhaled human or animal breath in 5 minutes.

In an exemplary embodiment, the collection point may be an un-patterned circular area at the center. For example, the un-patterned circular area may have a diameter of 8 mm, the grooves may be approximately 60 µm deep, the sampler may have an outer diameter of 20 mm, and the substrate may have a thickness of 500 µm. Alternatively, the collection point may be etched through the substrate so that it is open from the back side, which may allow a sample to be collected in a vial.

In experiments characterizing the surface of the sampler in a micro-analyzer having six sets of micro-patterned concentric rings or regions (with the geometry and the static contact angles summarized in Table 1), the contact angles of water droplets deposited on the surface of the sampler were measured with a goniometer. (However, in other embodiments, there may be fewer or more sets of micro-patterned concentric rings.) These contact angles were best described by Eqn. 3, i.e., the droplets deposited on the surface of the sampler are lifted by the micro-patterns. As discussed previously, the wettability gradient is distributed between the outer edge of the sampler surface (which is the most hydrophobic region) and the center collection point of the sampler (which is the least hydrophobic region). As a consequence, the measured contact angles on micropatterned regions decreased gradually from 157.0 to 126.7° (i.e., from the most hydrophobic to the least hydrophobic region) toward the center of the sampler surface. Moreover, the contact angle measured at the central collection point was 122°. (A greater range of differences can be achieved using similar techniques with nano-scale features.) The maximum measured contact-angle hysteresis ($\theta_R - \theta_A$) was approximately 1.8°. Thus, resistance for movement of droplets deposited on the surface was minimized.

TABLE 1

| Region | Position | Radius (µm) | Wall Width (µm) | Groove Width (µm) | Number of Groove and Wall Pairs | $\theta_e$ (°) |
|---|---|---|---|---|---|---|
| 1 | Inward | 4000 | 5.00 | 2.00 | 3590 | 126.7 |
|   | Outward | 5000 | 4.50 | 4.25 |  |  |
| 2 | Inward | 5000 | 5.00 | 6.50 | 2732 | 131.2 |
|   | Outward | 6040 | 4.50 | 9.30 |  |  |
| 3 | Inward | 5960 | 5.00 | 15.70 | 1821 | 139.4 |
|   | Outward | 7040 | 4.50 | 19.65 |  |  |
| 4 | Inward | 6960 | 5.00 | 31.23 | 1214 | 147.4 |
|   | Outward | 8040 | 4.50 | 36.90 |  |  |
| 5 | Inward | 7960 | 5.00 | 57.10 | 809 | 153.3 |
|   | Outward | 9040 | 4.50 | 65.36 |  |  |
| 6 | Inward | 8960 | 5.00 | 99.79 | 540 | 157.0 |
|   | Outward | 10000 | 4.50 | 111.94 |  |  |

(Note that, as illustrated in Table 1, the circular micro-patterned regions may be interconnected by overlapping one another, i.e. two consecutive regions may be chained as interlocking fingers.)

Moreover, motion of a series of purified water droplets (with sizes ranging from 2-10 µL) deposited with a syringe on the surface of the sampler was captured using a video camera. As a droplet was deposited on the surface it moved along the wettability gradient toward the center of the surface driven by the difference in capillary forces, which overcame the induced resistance force.

In additional experiments, the behavior of the sampler surface under condensation conditions was investigated. In condensation tests, the surface of the sampler was actively cooled using a thermoelectric cooler to 16 C, while the surrounding environment was at atmospheric pressure, an ambient temperature of 22.2 C, and a relative humidity of 48%. Initially, droplets nucleated on the surface without significant interactions among them. However, as the droplets grew in size, some of them coalesced and continued to grow in size to form larger droplets. After nucleation and initial growth, the droplets merged at their contact lines with other droplets. As the droplets coalesced, new nucleation sites became available, allowing new nuclei to grow. Moreover, as the condensation progressed, the droplets continued growing in size. Once they reached a critical size (e.g., when the droplets 'felt' the wettability gradient across their edges), they moved in a directional manner along the wettability gradient.

Thus, two forms of droplet sweeping took place during the condensation process on the micro-analyzer. During 'local sweeping,' nucleated droplets swept the surface as they grew in size and coalesced. Then, during 'radial sweeping,' larger droplets swept the surface and swallowed smaller droplets as they moved along the wettability gradient toward the collection point. This radial sweeping cleared the smaller droplets from the surface of the sampler, and therefore created new sites for droplet nucleation and growth. Because heat transfer is mostly suppressed at locations where droplets have diameters larger than 10 µm, the droplet sweeping on the micro-analyzer was effective in removing droplets from the surface during drop-wise condensation.

The preceding embodiments may include fewer components or additional components. For example, instead of the radial geometry described, the micro-analyzer may include a rectangular configuration of micro-pillars. Furthermore, instead of a trapezoidal cross-section, rectangular walls may be used in the radial geometry. Although these embodiments are illustrated as having a number of discrete items, these embodiments are intended to be functional descriptions of the various features that may be present rather than structural schematics of the embodiments described herein. Consequently, in these embodiments two or more components may be combined into a single component, and/or a position of one or more components may be changed.

Note that the micro-analyzer may be fabricated using an additive or positive process (i.e., a material-deposition process) and/or a subtractive or negative process (i.e., a material-removal process). For example, the process may include: sputtering, plating, isotropic etching, anisotropic etching, a photolithographic technique and/or a direct-write technique. Additionally, these processes may utilize a wide variety of materials, including: a semiconductor, metal, glass, sapphire, an organic material (such as polytetrafluoroethylene), a ceramic material, a plastic and/or silicon dioxide.

Figure 4:
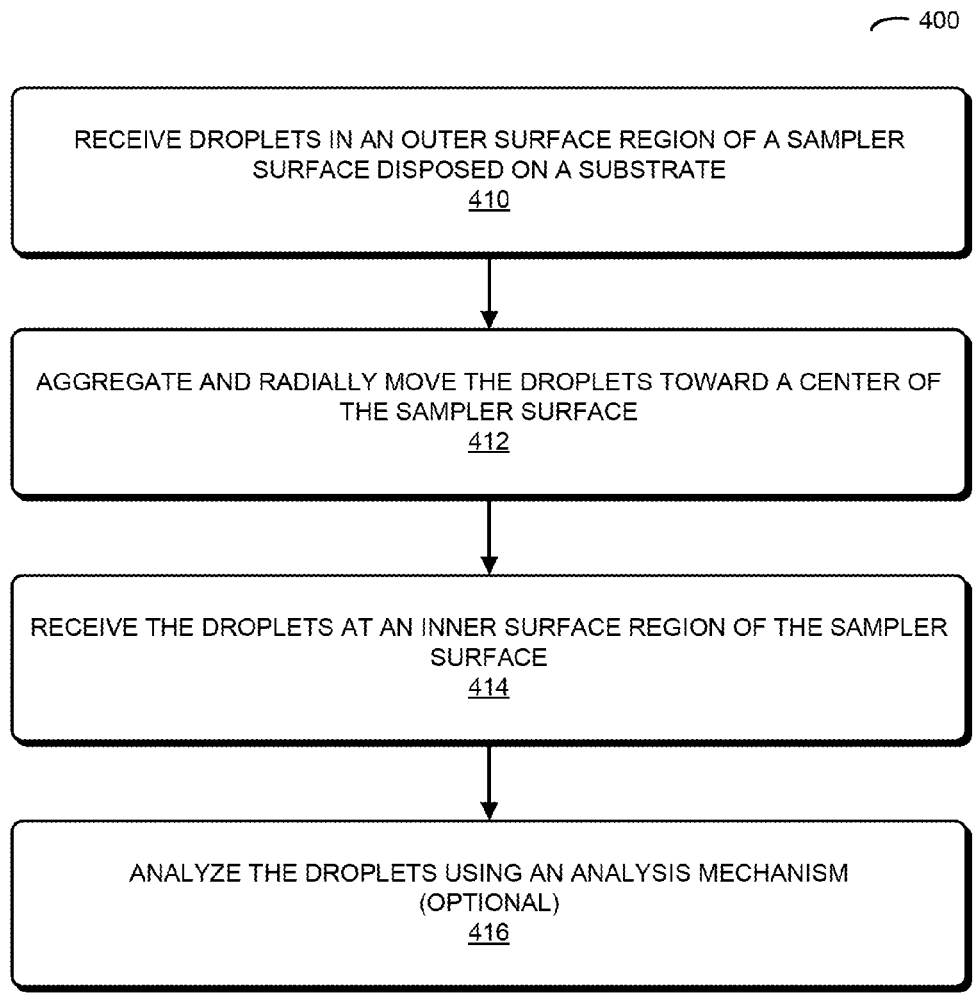
FIG. 4 is a flow chart illustrating a method for analyzing droplets in accordance with an embodiment of the present disclosure.

We now describe the method. FIG. 4 presents a flow chart illustrating a method 400 for analyzing droplets, which may be performed using micro-analyzer 100 (FIGS. 1 and 2). During this method, droplets are received in an outer surface region of a sampler surface disposed on a substrate (operation 410). Note that the sampler surface may be increasingly less hydrophobic along a radial direction toward the center of the sampler surface. For example, the outer surface region may be micro-patterned to create a wettability gradient which is distributed axisymmetrically.

Then, the droplets are aggregated and moved radially toward the center of the sampler surface (operation 412). This aggregation and motion may occur passively, i.e., a power source may not be used to transport the droplets on the sampler surface.

Next, the droplets are received at an inner surface region of the sampler surface (operation 414). Furthermore, the droplets are analyzed using an analysis mechanism (operation 416).

In some embodiments of method 400 there are additional or fewer operations. Moreover, the order of the operations may be changed, and/or two or more operations may be combined into a single operation.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A micro-analyzer configured for on-chip micro-analysis, comprising:
   a substrate;
   a patterned surface disposed on the substrate, which further comprises:
   an outer surface region configured to collect and transport liquid droplets radially toward a center of the patterned surface; and
   an inner surface region within the outer surface region, wherein the inner surface region is configured to receive the liquid droplets collected by the outer surface region; and
   an analysis mechanism in an area in the inner surface region configured to analyze the collected droplets,
   wherein the outer surface region comprises a set of micro-patterned concentric rings,
   wherein a given micro-patterned concentric ring from the set of micro-patterned concentric rings comprises a set of radially-oriented wall-groove pairs, and
   wherein the number of wall-groove pairs in the given micro-patterned concentric ring increases from an outermost ring toward an innermost ring.

2. The micro-analyzer of claim 1, wherein the patterned surface is configured so that the surface is increasingly less hydrophobic along a radial direction toward the center of the patterned surface.

3. The micro-analyzer of claim 1, wherein the outer surface region is micro-patterned to create a wettability gradient which is distributed axisymmetrically.

4. The micro-analyzer of claim 3, wherein the wettability gradient increases in an inward radial direction.

5. The micro-analyzer of claim 1, wherein the number of wall-groove pairs increases as the widths of grooves of the wall-groove pairs decrease from the outermost ring toward the innermost ring.

6. The micro-analyzer of claim 1, wherein the number of micro-patterned concentric rings is configured to control a wettability gradient of the outer surface region.

7. The micro-analyzer of claim 1, wherein a wall within a given wall-groove pair has a trapezoidal cross-section.

8. The micro-analyzer of claim 7, wherein a base of the wall has a varying width which increases in an inward radial direction.

9. The micro-analyzer of claim 1, further comprising a hydrophobic coating disposed on the outer surface region.

10. The micro-analyzer of claim 1, wherein the patterned surface receives a gas-phase sample that condenses into the liquid droplets.

11. The micro-analyzer of claim 10, wherein the outer surface region facilitates condensing of at least a component in the received gas-phase sample into the liquid droplets on the patterned surface.

12. The micro-analyzer of claim 1, wherein the substrate includes a silicon substrate.

\* \* \* \* \*